United States Patent [19]

Zoche et al.

[11] 3,932,535

[45] Jan. 13, 1976

[54] PROCESS FOR THE PREPARATION OF 2,2-BIS-(4-HYDROXY-3-CHLOROPHENYL)-PROPANE

[75] Inventors: Günter Zoche, Bonn-Beuel; Hermann Richtzenhain, Post Marialinden; Roshdy Ismail, Neunkirchen, all of Germany

[73] Assignee: Dynamit Nobel Aktiengesellschaft, Troisdorf, Germany

[22] Filed: Feb. 15, 1974

[21] Appl. No.: 442,939

Related U.S. Application Data

[60] Division of Ser. No. 261,827, June 12, 1972, Pat. No. 3,850,994, which is a continuation-in-part of Ser. No. 869,323, Oct. 24, 1969, abandoned.

[30] Foreign Application Priority Data

Sept. 15, 1969 Germany............................ 1946610
Oct. 30, 1968 Germany............................ 1805920

[52] U.S. Cl...... 260/619 A; 260/623 R; 260/623 H; 260/627 R
[51] Int. Cl.²......................................... C07C 37/22
[58] Field of Search........ 260/619 A, 623 H, 623 R, 260/619 R, 627 R

[56] References Cited
UNITED STATES PATENTS

| 2,254,904 | 9/1941 | Moss............................... 260/619 A |
| 2,812,365 | 11/1957 | Gump............................ 260/619 A |
| 3,673,262 | 6/1972 | Prehl.............................. 260/619 A |

Primary Examiner—James O. Thomas, Jr.
Assistant Examiner—W. B. Lone
Attorney, Agent, or Firm—Burgess, Dinklage & Sprung

[57] ABSTRACT

Process for the preparation of especially pure 2,2-bis-(4-hydroxy-3-chlorophenyl)-propane (dichlordiane, DCD) by the chlorination of 2,2-bis-(4-hydroxyphenyl)-propane in the presence of solvents that are substantially indifferent to chlorine by prior-art methods; then, for purification, the chlorinated bis-phenol is dissolved in halogenated hydrocarbons and/or halogenated hydrocarbon in which are liquid at 20°C which they are readily soluble in the absence of an aqueous phase but in which they are at most only slightly soluble after the addition of water thereto; and the 2,2-bis-(4-hydroxy-3-chlorophenyl)-propane, is thereby precipitated from this aqueous solution.

15 Claims, No Drawings

PROCESS FOR THE PREPARATION OF 2,2-BIS-(4-HYDROXY-3-CHLOROPHENYL)-PROPANE

This is a division, of application Ser. No. 261,827, filed June 12, 1972, which in turn is a continuation of Ser. No. 869,323 of Oct. 24, 1969 now abandoned.

It is in the prior art to chlorinte bisphenols, including 2,2-bis-(4-hydroxyphenyl)-propane (diane) to produce chlorinated products which have many known technical and commercial uses. In this known chlorination, chlorine atoms are rapidly taken up with the hydrogen atoms adjacent the two phenolic hydroxy groups being replaced by such chlorine. If certain known conditions of reaction are maintained, the dichlordiane (DCD) stage of chlorination can be realized in good yields using half the amount of chlorine necessary to produce tetrachlordiane (TCD).

This chlorination can be performed by a number of known methods. For example, the chlorination of diane by the use of chloroform, trichloroethylene, perchloroethylene and pentachloroethane has generally been described in Czech Pat. No. 106,367 (C.A. 60, 2834). In W. German Green Pat. No. 1,213,849 the use of aliphatic chlorinated hydrocarbons in the presence of water is described for this chlorination. Complete chlorination of diane to TCD with the use of 1,2-dichloroethane or glacial acetic acid as solvents is described in British Pat. No. 491,702, and with the use of carbon tetrachloride as the solvent in French Pat. No. 1,394,013.

In a process according to W. German Green Pat. No. 1,262,283 the complete chlorination of diane in benzene or toluene is described to be performed in the presence of water. Sulfuryl chloride has also been used for the chlorination of diane according to U.S. Pat. No. 2,902,518.

Chlorination to DCD can be performed by a number of known methods. For example, a description is given of the chlorination of diane using glacial acetic acid as the solvent in U.S. Pat. No. 2,455,652 and British Pat. No. 614,235, and using chloroform, trichloroethylene, perchloroethylene, and pentachloroethane in Czech Pat. No. 106,367 (C.A. 60, 2834 d). In W. German Green Pat. No. 1,213,849 a description is given of chlorination with the use of aliphatic chlorinated hydrocarbons in the presence of water (no example given for DCD). Also, sulfuryl chloride has already been used for the chlorination of diane, according to British Pat. No. 1,047,058 and USSR Pat. No. 145,584 (C.A. 57, 13 684 h).

The direct synthesis of DCD from o-chlorophenol and acetone is described in U.S. Pat. No. 2,455,703 and Zh. Obshch. Khim. 33, 487–90 (1963) (C.A. 59, 2732 c; 36% yield).

The purity of the TCD prepared by the prior-art methods varies, as it can be seen from the melting points stated in the above-named patents, ranging from 127° to 134.5°C for TCD and from 65° to 89.5°C for DCD. For many applications the degree of purity that has hitherto been achieved is entirely adequate. However, in the reaction of chlorinated dianes with bifunctional acid chlorides, such as dicarboxylic acid dichlorides, to form polyesters, it has been found that polyesters having only a relatively low molecylar weight can be obtained from the chlorinated dianes made by the prior-art methods. It has been found that these polyesters are not usable for the manufacture of sheet materials and the like. In order to make polyesters with a sufficiently high molecular weight, the dichlordiane or tetrachlordiane obtained by prior-art methods must additionally be subjected to purification either by recrystallization, which is as a rule expensive and wasteful, or by a process described in W. German Pat. No. 1,073,504. The purifying effect achieved by such procedures is sometimes hardly apparent from consideration of the melting point of the chlorinated dianes, but it is very substantially evident from the molecular weight of the polyesters made from them. Accordingly, the impurities which interfere with the manufacture of polyesters of high molecular weight cannot be determined with certainty from the melting point, so that the melting point is less useful as a criterion of purity than the measurement of the viscosity of the polyesters made from the chlorinated dianes.

It has now been found that pure dichlordiane and tetrachlordiane which are outstandingly suitable for the manufacture of polyesters of high molecular weight can be obtained very simply by the chlorination of 2,2-bis-(4-hydroxyphenyl)-propane in the presence of solvents which are substantially indifferent to chlorine by prior-art methods and then purifying the reaction product by dissolving such in a hydrocarbon or in one or more halogenated aliphatic hydrocarbons which are liquid at 20°C, and in which the product is easily soluble in the absence of an aqueous phase. Water is added to this solution which causes precipitation of the chlorinated diane in a purified condition.

The present invention is based upon the surprising observation that dichlordiane and tetrachlordiane can be precipitated in crystallized form from solution in certain hydrocarbon or halogenated hydrocarbons simply by the addition thereto of water or of an aqueous phase. The product crystals precipitated by the addition of water decompose merely on exposure to air or, more rapidly when they are dried, releasing the hydrocarbon or the halogenated hydrocarbon solvent and water, whereupon a modification of their crystal structure is clearly apparent. The product, free of water and solvent, is extremely well suited for the manufacture of polyesters of high molecular weight.

The effect of the reduction of this solubility in the hydrocarbon or the chlorinated hydrocarbon of both DCD and TCD by the addition of water to their solution is observed with a series of aliphatic halogenated hydrocarbons which are liquid at 20°C, such as methylene chloride, methyl iodide, ethyl bromide, trans-1,2-dichloroethylene, 1,2-dichloroethane, 1,2-dibromoethane, 1,4-dichlorobutane, and their homologs, etc.

Thus TCD (DCD) is soluble to 19.5% (28.7%) by weight at 18°C in 1,2-dichloroethane. After such a solution has been thoroughly mixed with water and the precipitate that develops has been separated, the 1,2-dichloroethane phase still contains only 3.5% by weight in the case of TCD, and only 2.3% by weight in the case of DCD.

The effect of the reduction of solubility is obtained in the case of dichlordiane also after the addition of water to a solution of the DCD in certain aromatic chlorinated or unchlorinated hydrocarbons, and also in chloroform and 1,1,2,2-tetrachloroethane.

For example, DCD is 40.0% soluble in benzene at 27°C. After such a solution has been mixed with water and the resultant precipitate has been separated, the benzene phase contains a remainder of only 10.9% dissolved DCD by weight. Mixtures of such solvents can also be used.

On the other hand, the solubility of the chlorinated dianes in other solvents, such as cyclohexane, chlorocyclohexane, chloroform, carbon tetrachloride, methyl chloroform and perchlorethylene, is not appreciably affected by the addition of water, so that these solvents are not as usable, or are entirely unusable, for the process according to the invention.

For the purification of TCD according to the invention, benzene, toluene, chlorobenzene chloroform and 1,1,2,2-tetrachloroethane are not suitable as solvents, either. halogenated hydrocarbons which are liquid at 20°C, such as methylene chloride, methyl iodide, ethyl bromide, trans-1,2-dichloroethlylene, 1,2-dichloroethane, 1,2-dibromoethane, 1,4-dichlorobutane, and their homologs, etc.

Thus TCD (DCD) is soluble to 19.5% (28.7%) by weight at 18°C in 1,2-dichloroethane. After such a solution has been thoroughly mixed with water and the precipitate that develops has been separated, the 1,2-dichloroethane phase still contains only 3.5% by weight in the case of TCD, and only 2.3% by weight in the case of DCD.

The effect of the reduction of solubility is obtained in the case of dichlordiane also after the addition of water to a solution of the DCD in certain aromatic chlorinated or unchlorinated hydrocarbons, and also in chloroform and 1,1,2,2-tetrachloroethane.

For example, DCD is 40.0% soluble in benzene at 27°C. After such a solution has been mixed with water and the resultant precipitate has been separated, the benzene phase contains a remainder of only 10.9% dissolved DCD by weight. Mixtures of such solvents can also be used.

On the other hand, the solubility of the chlorinated dianes in other solvents, such as cyclohexane, chlorocyclohexane, chloroform, carbon tetrachloride, methyl chloroform and perchlorethylene, is not appreciably affected by the addition of water, so that these solvents are not as usable, or are entirely unusable, for the process according to the invention.

For the purification of TCD according to the invention, benzene, toluene, chlorobenzene chloroform and 1,1,2,2-tetrachloroethane are not suitable as solvents, either.

However, although these solvents are not usable by themselves, they can be added even in high concentrations to those which are usable for the process of the invention.

The reduction in the solubility of the chlorinated dianes in the solvents that can be used according to the invention, which can be brought about by the addition of water, depends upon the temperature. The conditions necessary to achieve an optimum purifying effect may differ from case to case. It may be desirable to mix water into a solution of TCD at close to its boiling point, and to isolate the crystals that separate while it is hot. On the other hand, it may also be desirable to cool the solution after it has been mixed with water, and then separate the precipitated crystals.

The amount of water required for the precipitation of the chlorinated dianes from their solutions in a suitable chlorinated hydrocarbon can be varied over a wide range. It must be greater than the amount that is necessary to saturate the chlorinated hydrocarbon in question. The quantity of water is preferably determined by the desired composition of the crystalline precipitate formed after the addition of the water.

The crystals precipitated from a solution of TCD in 1,2-dichloroethane upon the addition of water preferably have approximately the following molar composition:

TCD : water : 1,2-dichloroethane = 1 : 3 – 4 : 0.5 – 0.7.

The crystals precipitated from a solution of DCD in 1,2-dichloroethane and in benzene upon the addition of water thereto have approximately the following molar compositions, respectively:

DCD : water : 1,2-dichloroethane = 1 : 2.5–3.5 : 0.6–0.8

DCD : water : benzene = 1 : 1.6–2.4 : 0.4–0.7.

It is possible that an inclusion compound is present since an excess of water over that which will yield the above compositions accomplishes nothing.

The preferred embodiment of the present invention resides in performing the chlorination of diane in a solvent which is substantially stable under the chlorination conditions and from which the chlorinated dianes can be precipitated by the addition of water. In this case it is only necessary to free the solution of hydrogen chloride, add water separate the precipitate which forms, and remove the water and solvent from the desired product. A TCD or DCD produced in this manner are already so pure that, in contrast to TCD or DCD prepared by prior-art methods, they can be used without further purification for the manufacture of polyesters of high molecular weight.

This embodiment differs quite substantially from the one described in W. German Pat. No. 1,213,849, in which the chlorination of bisphenols is performed in chlorinated hydrocarbons in the presence of 0.5 to 5% by weight water (percentage based upon the chlorinated hydrocarbon). The hydrogen chloride produced during the chlorination dissolves in the water present, forming concentrated hydrochloric acid. The produced concentrated hydrochloric acid is entirely indifferent to a solution of TCD in 1,2-dichloroethane, for example, and does not bring about the precipitation of TCD which can be achieved with water.

The process of the present invention will now be illustrated with the aid of the following examples which are not limiting on the scope hereof.

EXAMPLE 1

2280 g of diane (10 moles) were suspended in 5000 ml of 1,2-dichloroethane. Within 4 hours, 3190 g of chlorine (45 moles) were introduced with the exclusion of direct sunlight. After the temperature had autogenously risen to 60°C, it was maintained at this level by external cooling or heating as required. After the chlorination had ended, most of the dissolved hydrogen chloride, as well as a small excess of $Cl_2$, was driven out of the now clear solution with inert gas sparging.

To this solution, still at a temperature of 60°C, approximately 1000 ml of $H_2O$ was added. Crystallization began immediately. The solution was cooled down to 15°C in the course of 4 to 5 hours with stirring. An excellently filterable crystalline mass (diameter of crystals about 1 mm) was formed. The crystals were strongly suction-filtered, and carefully washed twice with 2000 ml of dichloroethane each time, and twice with 2000 ml of $H_2O$ each time. After drying at 80°C, a colorless, very pure TCD was obtained, having a melting point of 132.5° to 133.5°C. The yield amounted to 3100 g TCD (85% with reference to diane).

After concentration of the dichloroethane mother liquor and wash liquid, another 5% to 8% of a less pure TCD could be obtained by repeated precipitation with water. This TCD is advantageously added to the next batch prior to precipitation with water. In this manner, yields of very pure TCD amounting to better than 90% are obtained.

A polyester was prepared from the tetrachlorodiane thus obtained, by the following procedure:

In a three-necked flask provided with a stirrer, reflux condenser and gas introduction tube, 73.2 g of tetrachlorodiane, 20.3 g of terephthalic acid dichloride and 20.3 g of isophthalic acid dichloride were dissolved in 500 ml of o-dichlorobenzene, and the resultant solution was treated with 0.5 ml of quinoline and 0.5 ml of N,N-dimethylcyclohexylamine. The reaction mixture was heated with stirring to the boiling temperature of the o-dichlorobenzene. Reaction took place with evolution of hydrogen chloride. The reaction mixture was kept at its boiling temperature until the theoretical amount of hydrogen chloride had been produced.

The polyester thus obtained was precipitated by the addition of methanol, filtered and vacuum dried at about 200°C. The following characteristics were determined:

Yield: approx. 98% of the theory
| | |
|---|---|
| Stiffening Range | 340–360°C |
| Thermal stability according to Vicat (DIN 53,460): approx. | 235°C |
| Molecular weight determined by gel-chromatographic measurement: | $114 \times 10^3$ |
| Reduced viscosity: 1.3 (measured as 0.5 wt.% solution in chloroform at 25°C). | |

EXAMPLE 2

2 moles of diane were chlorinated as in Example 1 and the solution still at 60°C, was halved.

The one half was precipitated with water as described in Example 1, and washed twice each with 200 ml of water and 200 ml of carbon tetrachloride, respectively. 313 g of TCD resulted (85.5% of theoretical without treating the mother liquor), having a melting point of 132.5° to 133.5°C. The TCD thus obtained yielded a polyester having a reduced viscosity of 1.3 (determined as in Example 1).

The other half was allowed to cool slowly without the addition of water. A thick, very finely crystalline, difficultly filterable mass resulted, which was suction-filtered and twice washed with 200 ml of carbon tetrachloride. After drying, 153 g of TCD (41.8% of theoretical, without treating the mother liquor) was obtained, having a melting point of 132.5° to 133.5°C. The product obtained yielded a polyester by the process of Example 1, having a reduced viscosity of 1.1 (determined as in Example 1).

EXAMPLE 3

Chlorination in methylene chloride: 228 g of diane (1 mole) were suspended in 650 ml methylene chloride. Within 2.5 hours, 319 g of chlorine (4.5 moles) were introduced at about 40°C (apparatus as in Example 1). The pale yellow solution was sparged with nitrogen and was mixed with 100 ml of $H_2O$. The crystallization ended after 4 hours. The crystals were appreciably smaller than those obtained in accordance with Example 1; however, they were easily filterable. After suction-filtration, the product was washed twice each time with 250 ml methylene chloride, and then dried at 80°C. Thus, 320 g of TCD (87.4% of theoretical yield) were obtained, having a melting point of 132.5°–133.5°C. The resulting product yielded a polyester by the process of Example 1, having a reduced viscosity of 1.3 (determined as in Example 1).

EXAMPLE 4

A commercially obtainable TCD has a melting point of 131°–133.3°C, is yellowish, and has a strong odor of chlorinated monophenols. By the process of Example 1, a polyester having the following characteristics was made from this product:

| | |
|---|---|
| Stiffening Range: | 300–330°C |
| Vicat (DIN 53,460): | 192°C |
| Molecular weight, osmotically determined: | 27,000 |
| Reduced viscosity: | 0.7 (determined as in Ex. 1) |

With this commercial TCD, the following five purification experiments were performed:

a. 50 g of the TCD were dissolved in 68 ml of dichloroethane at 70°C and 14 ml of water were added. The mixture was let cool slowly to 20°C with stirring. The coarse crystals were suction-filtered and washed twice with 28 cm³ of carbon tetrachloride. After drying at 90°C, 46 g of pure TCD were obtained, having a melting point of 132.5° to 133.8°C, which corresponded to a yield of 92% (without treating the mother liquor). The polyester prepared from this as in Example 1 had a reduced viscosity of 1.3 (determined as in Example 1).

b. 50 g of the TCD was stirred at 20°C with 68 ml of dichloroethane and 14 ml of water. After 5 hours of stirring, the crystalline mass was suction-filtered, washed twice with 28 ml of carbon tetrachloride, and dried. The yield and melting point were identical with (a). The polyester prepared therefrom by the method of Example 1 had a reduced viscosity of 1.2 (determined as in Example 1).

c. 50 g of the TCD were dissolved in a mixture of 34 ml of 1,2-dichloroethane and 34 ml of cyclohexane at 65°C, and 14 ml of water was added. The mixture was allowed to cool to 20°C with stirring. The crystals were suctionfiltered and twice washed with 28 ml of the above mixture of solvents. After drying, 41.8 g of pure TCD were obtained, with a melting point of 133°C. Yield 83,6% without treating the mother liquor. The polyester prepared therefrom by the method of Example 1 had a reduced viscosity of 1.25 (determined as in Example 1).

d. 50 g of the TCD were dissolved in a mixture of 34 ml of 1,2-dichloroethane and 34 ml of perchloroethylene at 65°C, and 14 ml of water was added. The mixture was allowed to cool, with stirring, to about 20°C. The coarse crystals were suctionfiltered and washed twice with 28 ml of the above solvent mixture. After drying, 45.8 g of pure TCD were obtained, having a melting point of 132.5° to 133.5°C. Yield: 91.6% without treating the mother liquor. The polyester prepared therefrom by the method of Example 1 had a reduced viscosity of 1.3 (determined as in Example 1).

e. 50 g of the TCD were dissolved in a mixture of 13,5 ml of 1,2-dichloroethane and 54,5 ml of perchloroethylene at 70°C, and 14 ml of water was added. The mixture was allowed to cool, with stirring, to about 20°C. The coarse crystals were suction-filtered and washed twice with 28 ml of the above solvent mixture. After drying, 49,0 g of pure TCD were obtained, having a melting point of 132.5°to 133.5°C. Yield: 98% without treating the mother liquor. The polyester prepared therefrom by the method of Example 1 had a reduced viscosity of 1,3 (determined as in Example 1).

f. Recrystallization from benzene. 50 g of TCD were dissolved in 70 ml of heated benzene. Upon the slow cooling of the mixture a finely crystalline mass developed, which was suction-filtered, washed with 40 ml of carbon tetrachloride, and dried at 90°C. 40 g of TCD were obtained, M.P. 132.5° – 133.8°C, corresponding to an 80% yield (without treating the mother liquor). The polyester prepared therefrom by the method of Example 1 had a reduced viscosity of only 1,1 (determined as in Example 1).

EXAMPLE 5

2280 g of diane (10 moles) were suspended in 5000 ml of 1,2-dichloroethane at 20°C. Over a period of 2 hours, 1490 g of chlorine (21 moles) were introduced with the exclusion of direct sunlight, during which period the contents of the flask warmed to 60°C. After the chlorination was ended, inert gas was passed through the clear reaction solution to remove most of the hydrogen chloride still in solution.

About 1000 ml of water were added to this solution while it was still at 60°C, with stirring. Crystallization immediately commenced. The mixture was cooled to 15°C over the course of 4 to 5 hours. A very easily filterable crystalline mass developed. The crystals were strongly suctionfiltered, and carefully washed twice with 2000 ml of dichloroethane and twice with 2000 ml of water. Then they were dried. The drying temperature was at first kept at 45°C, and then gradually increased to 70°C. In this manner, a colorless, very pure, powdery DCD was obtained, having a melting point of 88° to 89°C. The yield amounted to 2827 g of DCD (95% of theoretical with reference to diane).

A polyaryl ester having a reduced viscosity of 1.47 and a melting range of 320°-340°C was obtained from this DCD with terephthalic acid dichloride, following the instructions given by S. V. Vinogradova, V. V. Korshak, P. M. Valetskii, A. N. Baskakov, and L. M. Gillman, in the Journal of Polymer Science of the U.S.S.R. (1967), pp. 1452-7.

S. V. Vinogradova et al (see above), using a differently prepared and repeatedly recrystallized DCD, obtained a polymer having a reduced viscosity of only 1.08 and a melting range of only 240°-250°C.

EXAMPLE 6 a. 297 g (1 mole) of DCD, M.P. 66°-72°C, produced according to Example 1 of U.S. Pat. No. 2,455,652, by the chlorination of diane in glacial acetic acid and one recrystallization from chloroform, was dissolved in 500 ml of 1,2-dichloroethane at 50°C, and stirred with 100 ml of water. The rest of the process was as described in Example 5 hereof. 284 g of a DCD, M.P. 88°-89°C were obtained, corresponding to a yield of 95.7% (without treating the mother liquor).

b. 297 g (1 mole) of the same DCD described as the starting material in a) were dissolved in 500 ml of benzene at 30°C and stirred with 100 ml of water. The rest of the procedure was as described in Example 5, except that the washing was done with only about 35% of the corresponding amount of cooled benzene.

179 g of pure DCD, M.P. 88°-89°C, were obtained, which corresponded to a yield of 60.3% (without treating the mother liquor).

c. 297 g (1 mole) of the same DCD, described as the starting material in a) were dissolved in a mixture of 250 ml 1,2-dichloroethane and 250 ml cyclohexane at 60°C and stirred with 100 ml of water. The rest of the procedure was as described in Example 5 except that the washing was done with a mixture of equal volumes of 1,2-dichloroethane and cyclohexane.

288 g of pure DCD, M.P. 88°-89°C were obtained, corresponding to a yield of 97% (without treating the mother liquor).

The purified DCD specimens of Examples 6(a) – (d), polymerized with terephthalic acid dichloride, yielded polymers having reduced viscosities of 1.48 and 1.56, respectively.

What is claimed is:

1. A process for the purification of 2,2-bis-(4-hydroxy-3-chlorophenyl)-propane obtained by chlorinating 2,2-bis-(4-hydroxyphenyl)-propane which comprises forming a solution of said 2,2-bis-(4-hydroxy-3-chlorophenyl)-propane by mixing the same with a solvent thereof selected from the group consisting of benzene, toluene, chlorobenzene, 1,1,2,2-tetrachloroethane, methylenechloride, methyliodide, ethylbromide, trans-1,2-dichloroethylene, 1,2-dichloroethane, 1,2-dibromoethane and 1,4-dichlorobutane, adding sufficient water thereto to form a precipitate of said 2,2-bis-(4-hydroxy-3-chlorophenyl)-propane, water and said solvent, which precipitate is insoluble in the remaining solvent, removing said precipitate from impurities which remain dissolved in the reaction mixture obtained from said chlorination and recovering 2,2-bis-(4-hydroxy-3-chlorophenyl)-propane from said precipitate.

2. A process according to claim 1 wherein said solvent is methyliodide.

3. A process according to claim 1 wherein said solvent is ethylbromide.

4. A process according to claim 1 wherein said solvent is trans-1,2-dichloroethylene.

5. A process according to claim 1 wherein said solvent is 1,2-dichloroethane.

6. A process according to claim 1 wherein said solvent is 1,2-dibromoethane.

7. A process according to claim 1 wherein said solvent is 1,4-dichlorobutane.

8. A process according to claim 1 wherein said solvent is benzene.

9. A process according to claim 1 wherein said solvent is toluene.

10. A process according to claim 1 wherein said solvent is chlorobenzene.

11. A process according to claim 1 wherein said solvent is 1,1,2,2-tetrachloroethane.

12. A process according to claim 1 wherein said solvent is methylene chloride.

13. A process according to claim 1 wherein said water is added in such proportions that the precipitated and crystalized phenolic compound has at least one of the following compositions: 2,2-bis-(4-hydroxy-3-chlorophenyl)-propane : 1.6–2.4 water : 0.4–0.7 benzene and benzene is the solvent employed.

14. A process according to claim 1 wherein the solvent employed is 1,2-dichloroethylene and the water is added in such proportions that the precipitated and crystallized phenolic compound has at least one of the following compositions: 2,2-bis-(4-hydroxy-3-chlorophenyl)-propane : 2.5–3.5 water: 0.6–0.8 1,2-dichloroethane.

15. A process according to claim 1 wherein the amount of water added to said solution is greater than that amount necessary to form a saturated aqueous solution of said solvent.

* * * * *

UNITED STATES PATENT AND TRADEMARK OFFICE
CERTIFICATE OF CORRECTION

PATENT NO. : 3,932,535
DATED : January 13, 1976
INVENTOR(S) : GÜNTER ZOCHE, HERMANN RICHTZENHAIN, ROSHDY ISMAIL It is certified that error appears in the above-identified patent and that said Letters Patent are hereby corrected as shown below:

[60] Change "continuation-in-part" to -- continuation --.

[57] Line 8, after "20°C" insert -- in --.

Column 3, line 14, delete "halogenated hydrocarbons which are liquid at";

cancel lines 15 through 47.

Signed and Sealed this twenty-second Day of June 1976

[SEAL]

Attest:

RUTH C. MASON
Attesting Officer

C. MARSHALL DANN
Commissioner of Patents and Trademarks